United States Patent [19]
Chiu et al.

[11] Patent Number: 5,218,138
[45] Date of Patent: Jun. 8, 1993

[54] STEREOSELECTIVE REDUCTION OF 3-HYDROXYKET-1-ONES TO 1,3-SYN-DIHYDROXYLATED COMPOUNDS

[75] Inventors: Fang-Ting Chiu, Lansdale; William L. Studt, Harleysville, both of Pa.

[73] Assignee: Rhone-Poulenc Rorer Pharmaceuticals Inc., Collegeville, Pa.

[21] Appl. No.: 939,273

[22] Filed: Sep. 2, 1992

[51] Int. Cl.$^5$ .............................................. C07C 69/76
[52] U.S. Cl. ...................................... 560/60; 554/125; 554/190; 554/213; 554/214; 554/218; 558/250; 564/170; 568/6
[58] Field of Search ............... 554/125, 190, 213, 214, 554/218; 560/60; 568/6; 564/170; 558/250

[56] References Cited

U.S. PATENT DOCUMENTS

| | | | |
|---|---|---|---|
| 2,712,527 | 7/1955 | Mikeska | 554/213 |
| 2,831,005 | 4/1958 | Walton | 554/213 |
| 4,248,889 | 2/1981 | Oka | 560/60 |
| 5,066,815 | 11/1991 | Sayo et al. | 560/60 |
| 5,093,363 | 3/1992 | Kita et al. | 560/60 |

FOREIGN PATENT DOCUMENTS

| | | |
|---|---|---|
| 6079642 | 6/1981 | Japan . |
| 1205229 | 9/1986 | Japan . |
| 1316341 | 12/1989 | Japan . |

*Primary Examiner*—Paul J. Killos
*Attorney, Agent, or Firm*—Raymond S. Parker; Martin F. Savitzky

[57] ABSTRACT

This invention is directed to a method for stereoselectively preparing a syn-dihydroxylated compound comprising reacting a 3-hydroxyket-1-one and a sterically hindered dialkylated borane to form a complex at about −50° C. to about 0° C., and reducing the complex with hydride at about −25° C. to about 50° C.

28 Claims, No Drawings

STEREOSELECTIVE REDUCTION OF 3-HYDROXYKET-1-ONES TO 1,3-SYN-DIHYDROXYLATED COMPOUNDS

FIELD OF THE INVENTION

This invention is directed to a method for stereoselectively reducing hydroxyketones to form chiral multihydroxylated compounds which are represented throughout biologically active compounds such as compactin, macrolides and particularly HMG-CoA inhibitors useful for the treatment of atherosclerosis, hyperlipidemia and hypercholesterolemia.

RECENT DEVELOPMENTS

The stereoselective reductions of 1,3-hydroxyketones to 1,3-syn dihydroxylated compounds using boranes or borinates in association with sodium borohydride is disclosed in the following references: K. Narasaka and F. C. Pai, Tetrahedron, 40, 2233 (1984); K. Prasad, et al., Tetrahedron Letters, 28, 155 (1987); K. Prasad, et al., Chem. Letters, 1923 (1987); T. R. Verhoeven, et al., Tetrahedron Letters, 26, 2951 (1985); W. Bartmann, et al., J. Med. Chem., 33, 61 (1990); D. R. Sliskovic, et al., J. Med. Chem., 33, 31 (1990); N. Balasubramanian, et al., J. Med. Chem., 32, 2038 (1989); G. E. Stokker, et al., J. Med. Chem., 28, 347 (1985); and J. E. Lynch et al., Tetrahedron Letters, 28, 1385 (1987). It is known also that S-hydroxy-β-acetic esters are stereoselectively reduced by means of zinc boronhydride, K. Prasad, et al., Helv. Chim. Acta, 69 803 (1986), or by means of sodium borohydride associated with an alkyl titanium while operating in tetrahydrofuran at $-78°$ C. These references disclose that in order to retain an appreciable degree of stereoselectiveness in the reductions that the reductions must be carried out at very low temperatures, e.g., at about $-100°$ C. to $-70°$ C.

S. Krishnamurthy and H. C. Brown, J. Org. Chem., 40(12), 1864 (1975) disclose that 9-borabicyclo[3.3.1]nonane (9-BBN) is an stabile dialkylborane that reduces aldehydes and ketones rapidly and cleanly to alcohols. The reference discloses also that 9-BBN hydroborates olefins with very high regio-and stereoselectivity. The reference does not disclose that 9-BBN may be used to effect the stereospecificity of a reduction.

It has been found that 1,3-syn-dihydroxylated compounds may be prepared from 1,3-hydroxyketones at higher temperatures while retaining a substantial degree of stereoselectiveness in the reduction. The present invention permits the reduction to be carried out in standard plant equipment obviating the need for special low temperature equipment, and at lower manufacturing cost.

SUMMARY OF THE INVENTION

The present invention is directed to a method for stereoselectively preparing a syn-dihydroxylated compound comprising reacting a 3-hydroxyket-1-one compound and a sterically hindered dialkylated borane to form a complex at about $-50°$ C. to about $0°$ C. in a solvent, and reducing the complex with hydride at about $-25°$ C. to about $50°$ C.

DETAILED DESCRIPTION OF THE INVENTION

As used above, and throughout the description of this invention, the following terms, unless otherwise indicated, shall be understood to have the following meanings:

The numbers "1" and "3" used in connection with the 1,3-dihydroxylated compound and 3-hydroxyket-1-one describe the relative hydrocarbon chain positions of the respective moieties to each other in the compounds.

"Alkyl" means a saturated aliphatic hydrocarbon group which may be straight or branched and having about 1 to about 20 carbon atoms in the chain. Branched means that a lower alkyl group such as methyl, ethyl, propyl, butyl or heptyl is attached to a linear alkyl chain. Preferred alkyl groups are the "lower alkyl" groups which are those alkyl groups having from 1 to about 8 carbons.

"Aryl" means phenyl or naphthyl or phenyl or naphthyl substituted with one or more aryl group substituents which may be the same or different, where "aryl group substituent" includes alkyl, aryl, hydroxy, alkoxy, aryloxy, aralkoxy, hydroxyalkyl, acyl, formyl, carboxy, aroyl, halo, nitro, trihalomethyl, cyano, alkoxycarbonyl, aryloxycarbonyl, aralkoxycarbonyl, acylamino, aroylamino, alkylsulfonyl, alkylsulfinyl, arylsulfonyl, arylsulfinyl, aralkylsulfonyl, aralkylsulfinyl, or -NRR' where R and R' are independently hydrogen, alkyl, aryl, or aralkyl.

"Cyclic alkyl" means a non-aromatic ring composed of about 6 to about 10 carbon atoms, and the cyclic alkyl may be partically unsaturated. Preferred cyclic alkyl rings include cyclopentyl, cyclohexyl, cycloheptyl, octahydronaphthyl and perhydronaphthyl. The cyclic alkyl may be optionally substituted with an aryl group substituent.

"Acyl" means an alkyl—CO— group. Lower acyl groups are preferred. Exemplary groups include acetyl, propanoyl, butanoyl and 2-methylbutanoyl.

"Aralkyl" means an aryl—alkyl— group. Lower alkyl are preferred. Exemplary groups are benzyl or phenethyl.

"Aralkoxy" means an aryl—alkyl—O— group. Lower alkyl are preferred. Exemplary groups are benzyloxy or phenethyloxy.

"Aroyl" means an aryl—CO— group. Exemplary groups include benzoyl, p-methylbenzoyl and 2-naphthoyl.

"Alkoxy" means an alkyl—O— group. Lower alkoxy groups are preferred. Exemplary groups include methoxy, ethoxy, n-propoxy, i-propoxy and n-butoxy.

"Aryloxy" means an aryl—O— group. Exemplary groups include phenoxy and 2-naphthyloxy.

"Akylthio" means an alkyl—S— group. Exemplary groups include methylthio and ethylthio.

"Alcohol" means HO—alkyl or HO—cyclic alkyl. Exemplary groups include methanol, ethanol, butanol, i-propanol, cyclopentanol and cyclohexanol.

"Alkoxyalkyl" means alkyl—O—alkyl or cyclic ether where the alkyl groups are taken together to form a ring having about 3 to about 8 carbon atoms. Exemplary alkoxyalkyls include diethyl ether, dibutyl ether, methyl t-butyl ether, tetrahydrofuran or tetrahydropyran "Alkylamino" means an amino group that is (mono- or di)alkylsubstituted. Exemplary groups include methylamine and diethylamine.

"Sterically hindered dialkylated borane" means a borane monohydride that is substituted with two bulky alkyl or cycloalkyl groups having about 5 to about 10 carbon atoms or with the two bulky groups taken together forming a bicyclic alkyl group. The sterically hindered dialkylated borane may be substituted optionally with aryl, aralkyl, aralkoxy, alkoxy, alkylthio or halide. Exemplary sterically hindered dialkylated boranes include 9-BBN, dicyclohexylborane or diamylborane.

"Halide" means flouride, chloride, bromide or iodide, and "Halo" means fluoro, chloro, bromo or iodo.

"Heterocyclyl" means about a 4- to about a 15- membered monocyclic or multicyclic ring system in which one or more of the atoms in the ring or rings is an element other than carbon, for example nitrogen, oxygen or sulfur. Preferred heterocyclyl groups include pyridinyl, 1,3-isoxazoly, isoquinolinyl, furanyl, imidizinyl and pyrrolinyl. The heterocyclyl may be optionally substituted with an aryl group substituent "Hydrophobic Radical" means hydrophobic alkyl, cyclic alkyl, aryl or heterocyclyl group. Assorted hydrophobic radicals are as exemplified in Table I. Methods for their preparation are disclosed in the following references: U.S. Pat. Nos. 4,459,422, 4,863,957, 5,001,144, 4,668,794, 4,647,576, 4,851,427, 4,613,610, 4,892,884, 4,868,185, 5,001,128, 4,946,860, 4,739,073, 4,804,679, 4,761,419, 4,870,187, 5,098,931; European Patent Nos.: 0, 326,386, 0,306,649; West German Patent No. DE 3,823,045; Heterocycles 29, 1497-1505 (1989); and PCT WO Publication No. 8,603,488. These references are incorporated herein by reference.

TABLE I

Examples of Hydrophobic Radicals

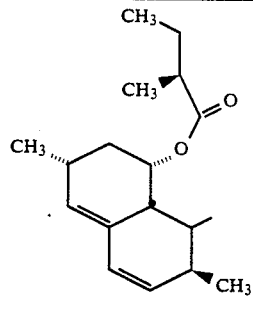

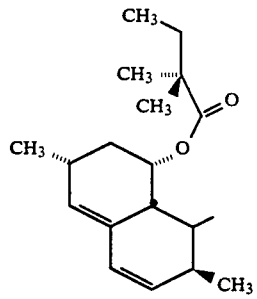

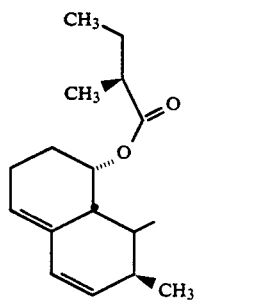

TABLE I-continued

Examples of Hydrophobic Radicals

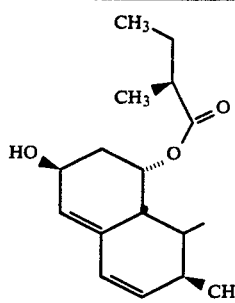

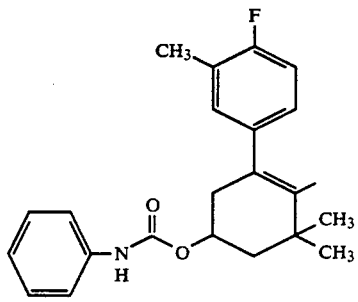

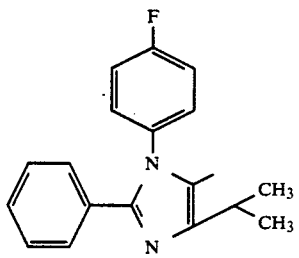

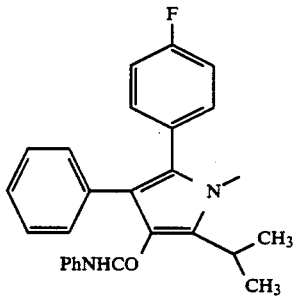

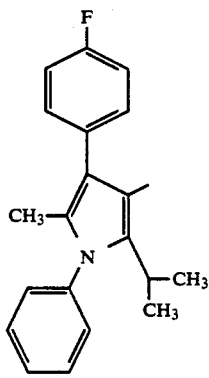

TABLE I-continued
Examples of Hydrophobic Radicals
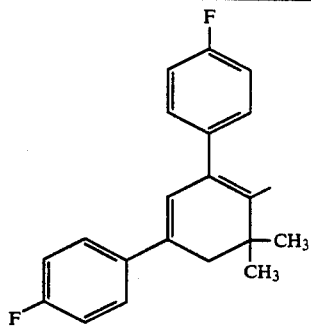
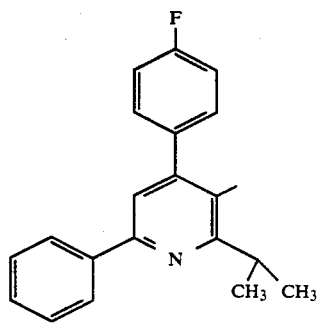
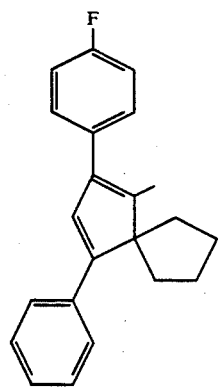
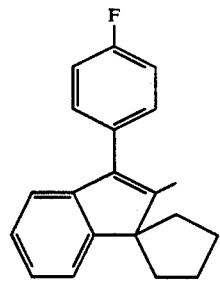
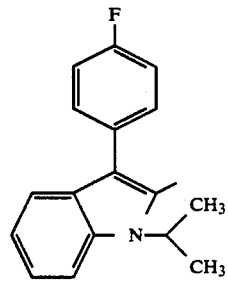
TABLE I-continued
Examples of Hydrophobic Radicals
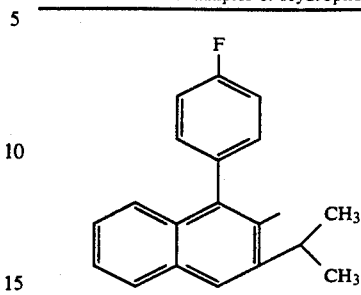
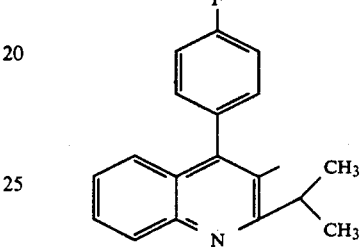
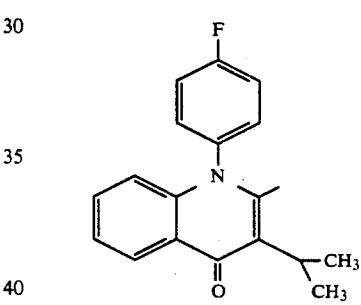
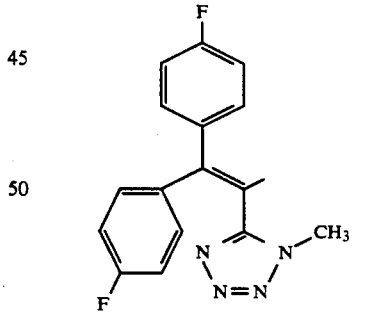
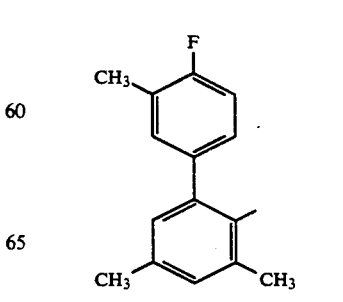

TABLE I-continued
Examples of Hydrophobic Radicals (Structures shown)

In the method according to the invention, the 3-hydroxyket-1-one may also be and is preferably reacted with a borane complexing agent and reacted subsequently with the sterically hindered dialkylated borane. The reaction the borane complexing agent is effected at about −50° C. to about 0° C.

A suitable sterically hindered dialkylated borane is selected from the group consisting of 9-BBN, dicyclohexylborane and diamylborane. 9-BBN is preferred.

A suitable borane complexing agent according to the method of this invention is selected from the group consisting of dialkylalkoxyborane or trialkylborane. The dialkylalkoxyborane is selected from the group consisting of methoxydiethylborane, ethoxydiethylborane, n-butoxydiethylborane, allyloxydiethylborane, i-propoxydiethylborane, t-butoxydiethylborane and methoxydin-butylborane. The most preferred dialkylalkoxyborane is methoxydiethylborane. The trialkylborane is selected from the group consisting of triethylborane, trii-butylborane, trin-butylborane and tricyclopentylborane. The preferred trialkylborane is triethylborane.

A suitable hydride according to the method of the invention is selected from the group consisting of sodium borohydride, potassium borohydride, lithium aluminum hydride, lithium trit-butoxyaluminum hydride, aluminum hydride and diborane. The preferred hydride is sodium borohydride or potassium borohydride.

It is particularly advantageous to use the sterically hindered dialkylated borane, borane complexing agent and hydride in about 1 to about 2 moles, about 0.5 to about 1 moles, and about 0.5 to about 1 moles respectively.

A suitable solvent for carrying out the method of the invention is an oxygen containing solvent selected from teh group consisting of alcohol, alkoxyalkyl, glyme, diglyme, polyalkyleneglycol and alkyl substituted polyalkyleneglycol. The solvent may be also a mixture of any of these solvents. The alkoxyalkyl is selected from the group consisting of tetrahydropyran, diethyl ether, dibutyl ether and methyl t-butyl ether. The glyme is selected from the group consisting of ethylene glycol monoethyl ether, 3-ethoxy-2-methyl-2-butanol, 3-methoxy-2-methyl-1-propanol, ethylene glycol mono-n-butyl ether and diethylene glycol monomethyl ether. The diglyme is selected from the group consisting of ethylene glycol dimethyl ether, ethylene glycol ethyl methyl ether, ethylene glycol methyl n-propyl ether, diethylene glycol dimethyl ether, diethylene glycol diethyl ether and triethylene glycol dimethyl ether. A suitable polyalkylene glycol has a molecular weight of about 200 to about 4000. Preferably, the polyalkylene glycol is a polyethylene glycol having a molecular weight of about 200 to 400, and more preferably the polyethylene glycol has a molecular weight of about 200. In addition, the polyalkylene glycol is a polypropylene glycol having a molecular weight of about 400 to 4000.

The method of the invention may also be and is preferably carried out in the presence of a hydrocarbon solvent. The hydrocarbon solvent is a $C_{4-15}$ aliphatic compound or $C_{6-12}$ aryl compound. The $C_{4-15}$ aliphatic compound is selected from the group consisting of heptane, 2-methylpropane, trans-1,2-dimethylcyclopentane, spiropentane, cis-1,4-dimethylcyclohexane, decane, n-dodecane and cycloheptane. Heptane is preferred. The $C_{6-12}$ aryl compound is selected from the group consisting of benzene, toulene, xylene, mesitylene, tetralin, 2-ethylnaphthalene and p-cymene. Benzene is preferred.

It is particularly advantageous to utilize the hydrocarbon and oxygen containing solvent in a ratio of about 10 to about 90% volume of the hydrocarbon solvent to about 90 to about 10% volume of the oxygen containing solvent. The mixture of heptane and polyethyleneglycol having a molecular weight of about 200 is preferred.

The temperature range for forming the complex is dependent on the choice of the sterically hindered dialkylated borane. The preferred temperature range is at temperatures from about $-10°$ C. to about $-50°$ C; and more preferably from about $-20°$ C. to about $-50°$ C. and further, preferably at about $-30°$ C. to about $-50°$ C. The preferred temperature range for reducing the complex is about $-25°$ C. to about $25°$ C; and more preferably from about $-25°$ C. to about $10°$ C. and further, preferably at about $-25°$ C. to about $-10°$ C.

A preferred syn-1,3-dihydroxylated compound prepared using the present invention has the formula

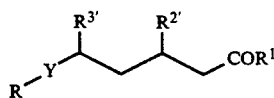

wherein
Y is —C≡C—, —(CH$_2$)$_a$— or —(CH$_2$)$_b$CH=CH(CH$_2$)$_c$—;
a is 1,2 or 3;
b and c are independently 0 or 1, provided that when one of b and c is 1 then the other of b and c is 0 and both of b and c are not 0;
R is a hydrophobic radical;
$R^1$ is hydroxy, alkoxy, cycloalkoxy, aryloxy, heteroaryloxy, alkylthio, amino or alkylamino; and
$R^{2'}$ and $R^{3'}$ are hydroxy, and $R^{2'}$ and $R^{3'}$ taken together form a bi-fused moiety of the formula

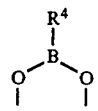

wherein $R^4$ is alkyl, alkoxy, or cycloalkyl. More preferred is the compound wherein Y is —(CH$_2$)$_a$—; a is 1; $R^1$ is alkoxy; and $R^{2'}$ and $R^{3'}$ are hydroxy. The compound wherein the hydrophobic radical is selected from the group consisting of 2-(4-fluorophenyl)-4,4,6,6-tetramethyl-1-cyclohexen-1-yl, 2-(4-fluoro-3-methylphenyl)-4,4,6,6-tetramethyl-1-cyclohexen-1-yl and (4-flourophenyl)-2-isopropyl-1-oxo-1,2-dihydroisoquinol-3-yl is also preferred.

A preferred 3-hydroxyket-1-one that is reduced using the method of the present invention has the formula

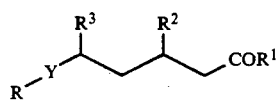

wherein
Y is —C≡C—, —(CH$_2$)$_a$— or —(CH$_2$)$_b$CH=CH(CH$_2$)$_c$—;
a is 1, 2 or 3;
b and c are independently 0 or 1, provided that when one of b and c is 1 then the other of b and c is 0 and both of b and c are not 0;
R is a hydrophobic radical;
$R^1$ is hydroxy, alkoxy, cycloalkoxy, aryloxy, heteroaryloxy, alkylthio, amino or alkylamino; and
$R^2$ and $R^3$ are independently hydroxy or =O, provided that $R^2$ and $R^3$ are not both hydroxy or =O. More preferred is the compound wherein Y is —(CH$_2$)$_a$—; a is 1; $R^1$ is alkoxy; $R^2$ is =O; and $R^3$ is hydroxy. The compound wherein the hydrophobic radical is selected from the group consisting of 2-(4-fluorophenyl)-4,4,6,6-tetramethyl-1-cyclohexen-1-yl, 2-(4-fluoro-3-methylphenyl)-4,4,6,6-tetramethyl-1-cyclohexen-1-yl and (4-fluorophenyl)-2-isopropyl-1-oxo-1,2-dihydroisoquinol-3-yl is also preferred.

In particular, the 3-hydroxyket-1-one of the formula

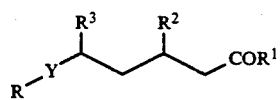

is obtained by usual methods such as the reaction of an aldehyde of the general formula

R—CHO wherein R is as defined above with the dianion of a derivative of acetylacetic acid of the general formula

CH$_3$COCH$_2$COR$^1$ wherein $R^1$ is as defined above and preferably is alkoxy, or with an anion of a acetic compound of the general formula

CH$_3$—CO—R$^1$ wherein Z is as defined above and preferably is alkoxy.

The 1,3-dihydroxylated product is isolated according to standard techniques such as purification by chromatography.

In the method according to the invention the product from the reduction of the complex wherein $R^{2'}$ and $R^{3'}$ taken together form a bi-fused moiety of the formula

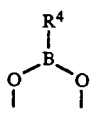

may be treated under standard acid or oxidation conditions to convert $R^{2'}$ and $R^{3'}$ to hydroxy.

According to the method of this invention the syn-dihydroxylated compound is prepared substantially free of its anti-isomer. Preferably the syn-dihydroxylated compound is prepared in a radio of greater than about 3 to 1 to its anti-isomer, more preferably in a ratio of greater than about 6 to 1 to its anti-isomer, and further preferably in a ratio of greater than about 12 to 1 to its anti-isomer. It should be understood that the temperature at which the complex is formed is related to the relative amounts of the syn and anti-isomer produced according to this invention. At the lower temperature ranges described hereinbelow, the syn/anti-ratio is greater than at the higher temperature used in the present invention. Nonetheless, the present invention results in a significantly higher syn/anti-ratio at any particular temperature in comparison to the isomeric ratios obtained utilizing the prior art methods.

The present invention is further exemplified but not limited by the following illustrative examples.

EXAMPLE 1

A solution of methyl 7-[2-(4-fluoro-3-methylphenyl)-4,4,6,6-tetramethyl-1-cyclohexe-1-yl]-5-hydroxy-3-oxo-heptenoate (1 mole) in tetrahydrofuran (THF) is treated with $Et_2B(OMe)$ (1 mole) and then treated with 9-BBN (1.03 mole). After stirring at $-20°$ C. for 1 hour, the suspension is treated with 2.0M $NaBH_4$ (0.9 mole) in triglyme solution. After 30 minutes stirring, the mixture is quenched with $NH_4Cl$ solution and extracted with heptane. The heptane layer is concentrated to yield over 94% of methyl 7-[2-(4-fluoro-3-methylphenyl)-4,4,6,6-tetramethyl1-cyclohexe-1-yl]-3,5-dihydroxyheptenoate with 13.2–14.0/1.0 syn/anti ratio.

EXAMPLE 2

The data in Table II below presents comparative results obtained when methyl 7-[2-(-4-fluoro-3-methylphenyl)-4,4,6,6-tetramethyl-1-cyclohexen-1-yl]-5-hydroxy-3-oxo-6-heptenoate, is reduced without a sterically hindered dialkylated borane and with sodium borohydride to yield the 1,3-dihydroxylated compound, methyl 7-[2-(4-fluoro-3-methylphenyl)-4,4,6,6-tetramethylcyclohex-1-yl]-3,5-dihydroxyhepten-6-oate, under the identified conditions.

TABLE II

| | Reduction with Sodium Borohydride | | |
|---|---|---|---|
| Complexing Agent/ Amount $Et_2BOMe$ | Temperature (°C.) | Solvent | Isolation of 1,3-dihydroxylated Compound: Syn/Anti |
| 0.3 | −11 | THF/MeOH | 3/1 |
| 0.3 | −20 | THF/MeOH | 3.9/1 |
| 0.3 | −40 | THF/MeOH | 5.6/1 |

TABLE II-continued

| | Reduction with Sodium Borohydride | | |
|---|---|---|---|
| Complexing Agent/ Amount $Et_2BOMe$ | Temperature (°C.) | Solvent | Isolation of 1,3-dihydroxylated Compound: Syn/Anti |
| 1.6 | −11 | THF/MeOH | 4.2–5.7/1 |
| 1.6 | −20 | THF/MeOH | 5.4–6.9/1 |
| 1.6 | −12 | Monoglyme/MeOH | 6.7/1 |
| 1.6 | −12 | Diglyme/MeOH | 8.7/1 |
| 1.6 | −12 | Diglyme/heptane | 5.9/1 |
| 1.6 | −10 ± 5° C. | Diglyme | 7.7/1 |
| 1.6 | −20 | Heptane/MeOH | 5.3/1 |
| 1.0 | −5 | PEG/Heptane | 8.3/1 |
| 1.0 | −20 | PEG/Heptane | 8.4/1 |
| 1.0 | −35 | PEG/Heptane | 8.1/1 |
| 1.0 | 2 | PEG/Heptane | 6.5/1 |
| 1.0 | 15 | PEG/Heptane | 6.6/1 |

What is claimed is:

1. A method for stereoselectively preparing a syn-dihydroxylated compound comprising reacting a 3-hydroxyket-1-one and a sterically hindered dialkylated borane to form a complex at about $-50°$ C. to about $0°$ C., and reducing the complex with hydride at about $-25°$ C. to about $50°$ C.

2. The method of claim 1 wherein said syn-dihydroxylated compound is prepared substantially free of its anti-isomer.

3. The method of claim 2 wherein the ratio of syn- to anti-isomer is greater than about 6 to 1.

4. The method of claim 3 wherein the ratio of syn- to anti-isomer is greater than about 12 to 1.

5. The method of claim 1 wherein said sterically hindered dialkylated borane is selected from the group consisting of 9-borabicyclo[3.3.1]nonane, dicyclohexylborane and diamylborane.

6. The method of claim 5 wherein said sterically hindered dialkylated borane is 9-borabicyclo[3.3.1]nonane.

7. The method of claim 1 further comprising reacting initially said 3-hydroxyket-1-one with a borane complexing agent.

8. The method of claim 7 wherein said borane complexing agent is selected from the group consisting of dialkylalkoxyborane and trialkylborane.

9. The method of claim 8 wherein said dialkylalkoxyborane is selected from the group consisting of methoxydiethylborane, ethoxydiethylborane, n-butoxydiethylborane, allyloxydiethylborane, isopropoxydiethylborane, t-butoxydiethylborane and methoxydin-butylborane.

10. The method of claim 9 wherein said dialkylalkoxyborane is methoxydiethylborane.

11. The method of claim 10 wherein said trialkylborane is selected from the group consisting of trii-butylborane, trin-butylborane and tricyclopentylborane.

12. The method of claim 11 wherein said trialkylborane is triethylborane.

13. The method of claim 1 wherein solvent is selected from the group consisting of alcohol, alkoxyalkyl, glyme, diglyme, polyalkyleneglycol and alkyl substituted polyalkyleneglycol.

14. The method of claim 13 wherein said polyalkylene glycol has a molecular weight of about 200 to about 4000.

15. The method of claim 14 wherein said polyethylene glycol has a molecular weight of about 200.

16. The method of claim 1 wherein said 3-hydroxy-ket-1-one is reduced under conditions further comprising the presence of a hydrocarbon solvent.

17. The method of claim 16 wherein said hydrocarbon solvent is a $C_{4-15}$ aliphatic compound or $C_{6-12}$ aryl compound.

18. The method of claim 17 wherein said $C_{4-15}$ aliphatic compound is heptane.

19. The method of claim 1 wherein said hydride is selected from the group consisting of sodium borohydride, potassium borohydride, lithium aluminum hydride, lithium trit-butoxyaluminum hydride, aluminum hydride, dii-butylaluminum hydride and diborane.

20. The method of claim 19 wherein said hydride is sodium borohydride or potassium borohydride.

21. The method of claim 1 wherein said reducing is at about $-25°$ C. to about $-10°$ C.

22. The method of claim 1 wherein said reacting is at about $-50°$ C. to about $-30°$ C.

23. The method of claim 1 wherein said 3-hydroxy-ket-1-one is of the formula

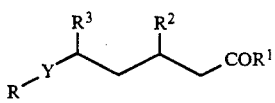

wherein
Y is —C≡C—, —(CH$_2$)$_a$— or —(CH$_2$)$_b$CH=CH(CH$_2$)$_c$—;
a is 1, 2 or 3;
b and c are independently 0 or 1, provided that when one of b and c is 1 then the other of b and c is 0 and both of b and c are not 0;
R is a hydrophobic radical;
$R^1$ is hydroxy, alkoxy, cycloalkoxy, aryloxy, heteroaryloxy, alkylthio, amino or alkylamino; and
$R^2$ and $R^3$ are independently hydroxy or =O, provided that $R^2$ and $R^3$ are not both hydroxy or =O.

24. The method of claim 23 wherein
Y is —(CH$_2$)$_a$—;
a is 1;
$R^1$ is alkoxy;
$R^2$ is =O; and
$R^3$ is hydroxy.

25. The method of claim 24 wherein said hydrophobic radical is 2-(4-fluorophenyl)-4,4,6,6-tetramethyl-1-cyclohexen-1-yl, 2-(4-fluoro-3-methylphenyl)-4,4,6,6-tetramethyl-1-cyclohexen-1-yl or (4-fluorophenyl)-2-isopropyl-1-oxo-1,2-dihydroisoquinol-3-yl.

26. The method of claim 1 wherein said dihydroxylated compound is of the formula

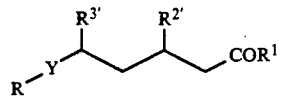

wherein
Y is —C≡C—, —(CH$_2$)$_a$— or —(CH$_2$)$_b$CH=CH(CH$_2$)$_c$—;
a is 1, 2 or 3;
b and c are independently 0 or 1, provided that when one of b and c is 1 then the other of b and c is 0 and both of b and c are not 0;
R is a hydrophobic radical;
$R^1$ is hydroxy, alkoxy, cycloalkoxy, aryloxy, heteroaryloxy, alkylthio, amino or alkylamino; and
$R^{2'}$ and $R^{3'}$ are hydroxy, and $R^{2'}$ and $R^{3'}$ taken together form a bi-fused moiety of the formula

wherein $R^4$ is alkoxy, alkyl or cycloalkyl.

27. The method of claim 26 wherein
Y is —(CH$_2$)$_a$—;
a is 1;
$R^1$ is alkoxy; and
$R^{2'}$ and $R^{3'}$ are hydroxy.

28. The method of claim 27 wherein said hydrophobic radical is selected from the group consisting of 2-(4-fluorophenyl)-4,4,6,6-tetramethyl-1-cyclohexen-1-yl, 2-(4-fluoro-3-methylphenyl)-4,4,6,6-tetramethyl-1-cyclohexen1-yl and (4-fluorophenyl)-2-isopropyl-1-oxo-1,2-dihydroisoquinol-3-yl.

* * * * *